US009999437B2

(12) United States Patent
Kesten et al.

(10) Patent No.: US 9,999,437 B2
(45) Date of Patent: Jun. 19, 2018

(54) METHOD AND APPARATUS FOR FORMING OPENING IN A SINUS WALL

(71) Applicant: Acclarent, Inc., Menlo Park, CA (US)

(72) Inventors: Randy J. Kesten, Mountain View, CA (US); Jessica M. Liberatore, San Mateo, CA (US); Thomas R. Jenkins, Alameda, CA (US)

(73) Assignee: Acclarent, Inc., Irvine, CA (US)

( * ) Notice: Subject to any disclaimer, the term of this patent is extended or adjusted under 35 U.S.C. 154(b) by 662 days.

(21) Appl. No.: 14/469,841

(22) Filed: Aug. 27, 2014

(65) Prior Publication Data
US 2016/0058462 A1    Mar. 3, 2016

(51) Int. Cl.
| A61B 17/32 | (2006.01) |
| A61B 1/00 | (2006.01) |
| A61B 1/233 | (2006.01) |
| A61B 1/32 | (2006.01) |
| A61F 5/08 | (2006.01) |
| A61B 17/24 | (2006.01) |
| A61B 17/3205 | (2006.01) |
| A61B 90/00 | (2016.01) |

(52) U.S. Cl.
CPC .. *A61B 17/320016* (2013.01); *A61B 1/00082* (2013.01); *A61B 1/00087* (2013.01); *A61B 1/00183* (2013.01); *A61B 1/233* (2013.01); *A61B 1/32* (2013.01); *A61B 17/24* (2013.01); *A61B 17/32053* (2013.01); *A61F 5/08* (2013.01); *A61B 90/03* (2016.02)

(58) Field of Classification Search
CPC ...... A61B 17/320016; A61B 17/32002; A61B 18/1445; A61B 17/32053; A61B 17/1604; A61B 17/24; A61B 1/233; A61B 1/32; A61B 90/03; A61F 5/08
USPC .......................... 606/79, 167, 170, 184, 185
See application file for complete search history.

(56) References Cited

U.S. PATENT DOCUMENTS 5,335,671 A * 8/1994 Clement ................ A61B 10/04
                                                    600/566
5,665,072 A * 9/1997 Yoon .................. A61B 17/3417
                                                    604/164.12

(Continued)

FOREIGN PATENT DOCUMENTS

WO    WO 2010/078145 A1    7/2010

OTHER PUBLICATIONS

PCT International Search Report for PCT/US15/044622 dated Feb. 28, 2017.*

(Continued)

*Primary Examiner* — Katherine M Shi
(74) *Attorney, Agent, or Firm* — Frost Brown Todd LLC

(57) ABSTRACT

An instrument comprises a shaft assembly. The shaft assembly comprises a first shaft member including a distal cutting feature, and a second shaft member. The first shaft member is slidable relative to the second shaft member. At least a distal portion of the shaft assembly is sized to fit through a nostril. The instrument further comprises a body. At least a portion of the shaft assembly extends distally relative to the body. The body comprises a grounding feature sized and positioned to engage one or more external anatomical structures adjacent to the nostril. The instrument further comprises a dampener. The dampener resists advancement of the first shaft member relative to the second shaft member.

19 Claims, 11 Drawing Sheets

(56) References Cited

U.S. PATENT DOCUMENTS

| | | | |
|---|---|---|---|
| 6,080,176 A * | 6/2000 | Young | A61B 17/32053 |
| | | | 606/180 |
| 6,554,845 B1 | 4/2003 | Fleenor et al. | |
| 7,654,997 B2 | 2/2010 | Makower et al. | |
| 9,155,492 B2 | 10/2015 | Jenkins et al. | |
| 2003/0135237 A1* | 7/2003 | Cragg | A61B 17/0057 |
| | | | 606/213 |
| 2010/0030031 A1 | 2/2010 | Goldfarb et al. | |
| 2011/0004057 A1 | 1/2011 | Goldfarb et al. | |
| 2014/0277043 A1 | 9/2014 | Jenkins et al. | |

OTHER PUBLICATIONS

U.S. Appl. No. 61/725,523, filed Nov. 13, 2012.
International Search Report dated Dec. 2, 2015 for Application No. PCT/US2015/044622, 3 pgs.

* cited by examiner

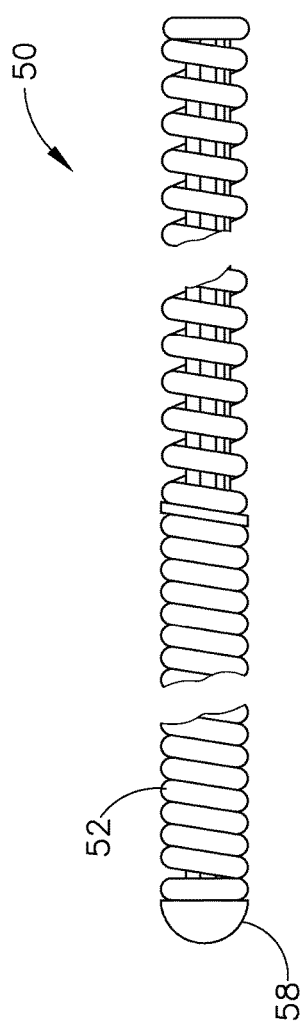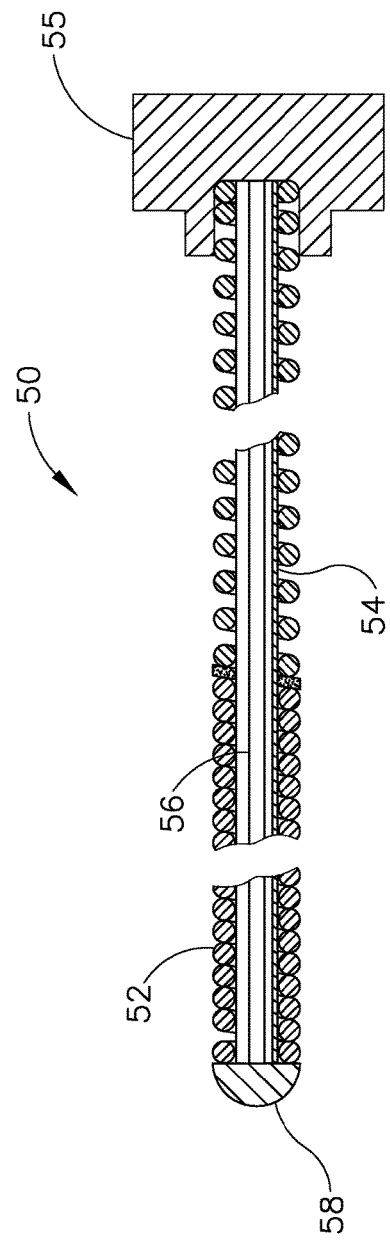

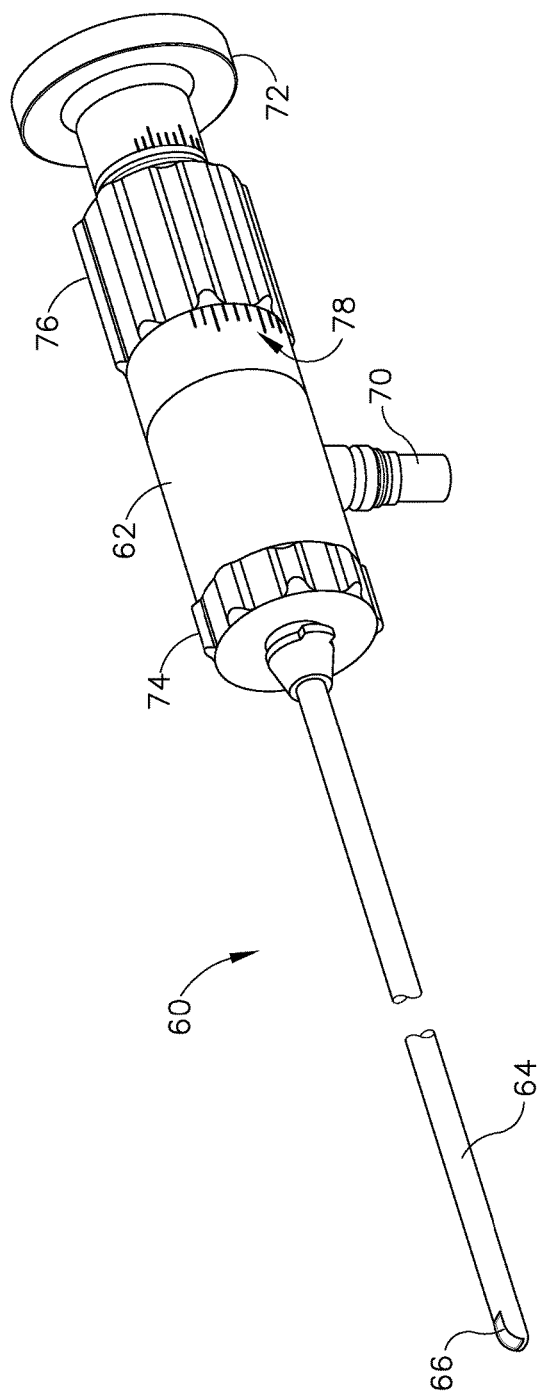
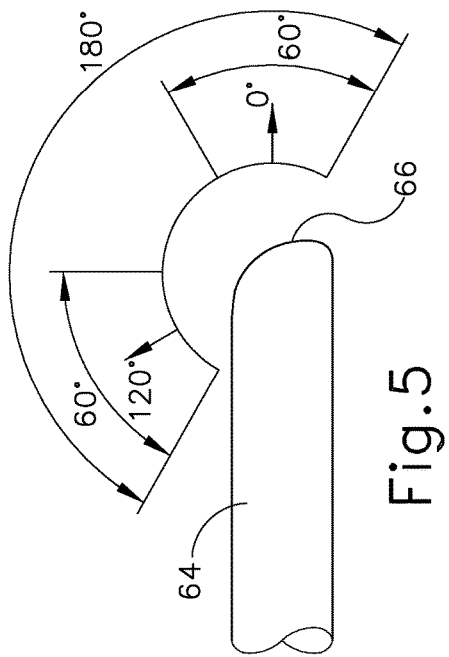
Fig.4
Fig.5

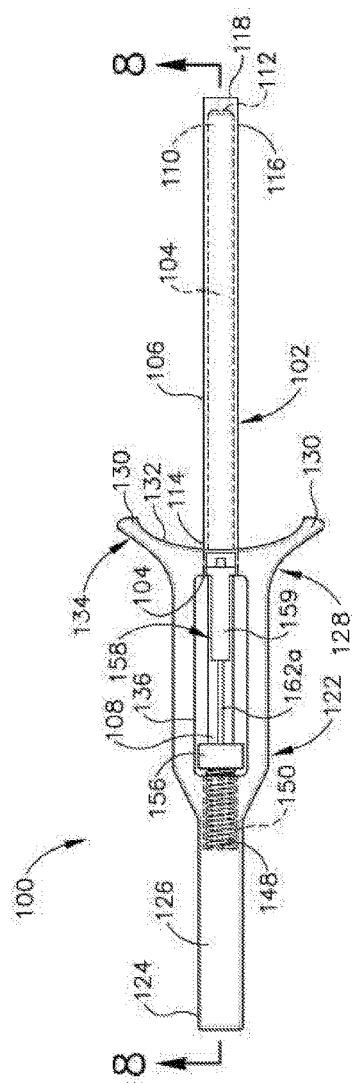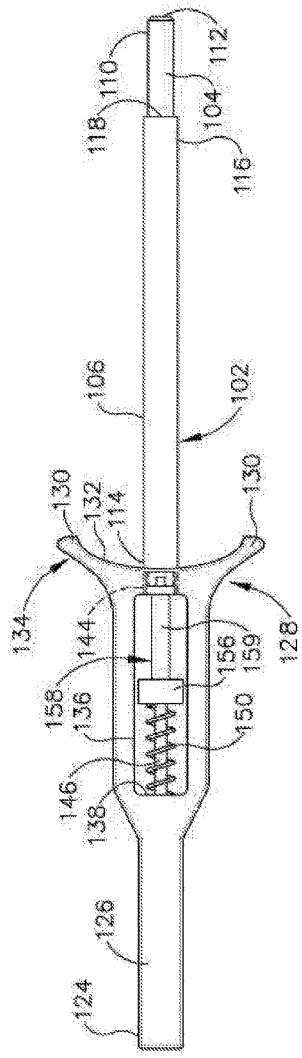
Fig.7A
Fig.7B

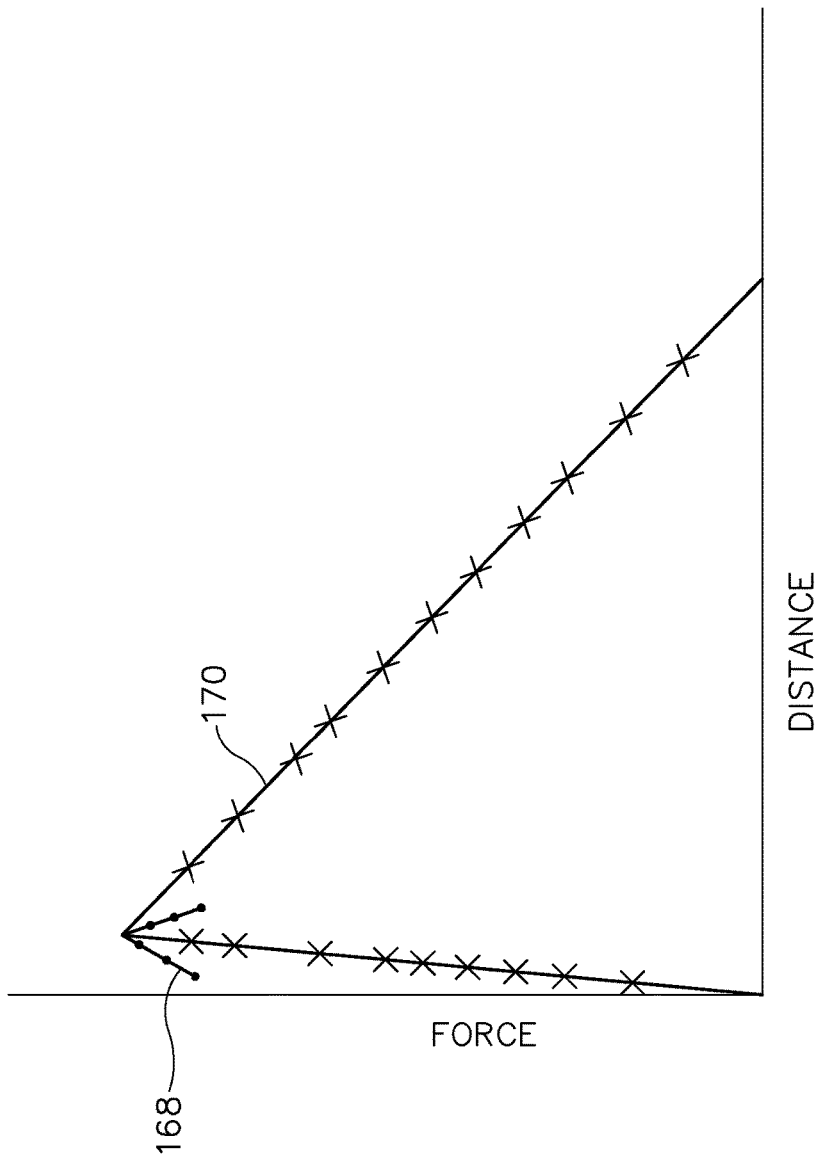

METHOD AND APPARATUS FOR FORMING OPENING IN A SINUS WALL

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of an exemplary illuminating guidewire suitable for use with the dilation catheter system of FIG. 1;

FIG. 3 depicts a side cross-sectional view of the illuminating guidewire of FIG. 2;

FIG. 4 depicts a perspective view of an exemplary endoscope suitable for use with the dilation catheter system of FIG. 1;

FIG. 5 depicts a side elevational view of the distal end of the endoscope of FIG. 5, showing an exemplary range of viewing angles;

FIG. 7A depicts a side elevational view of an exemplary instrument for piercing a wall of the ethmoid bulla, with a cutting feature in a retracted position;

FIG. 7B depicts a side elevational view of an exemplary instrument for piercing a wall of the ethmoid bulla, with the cutting feature in an extended position;

FIG. 11 depicts an exemplary force-distance plot associated with an instrument for piercing a wall of the ethmoid bulla.

Figure 1:
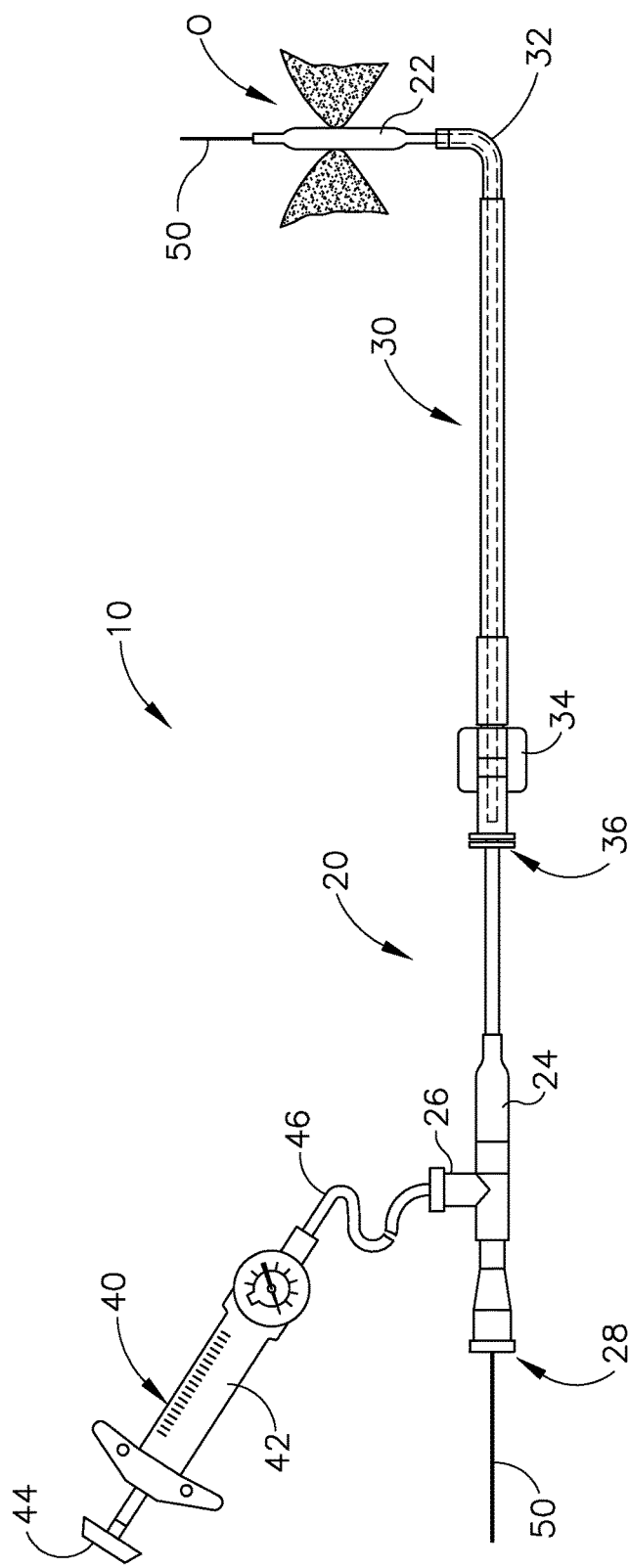
FIG. 1 depicts a side elevational view of an exemplary dilation catheter system.

The drawings are not intended to be limiting in an way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw thud from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables as viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Instrument for Piercing a Wall of the Ethmoid Bulla

Figure 6:
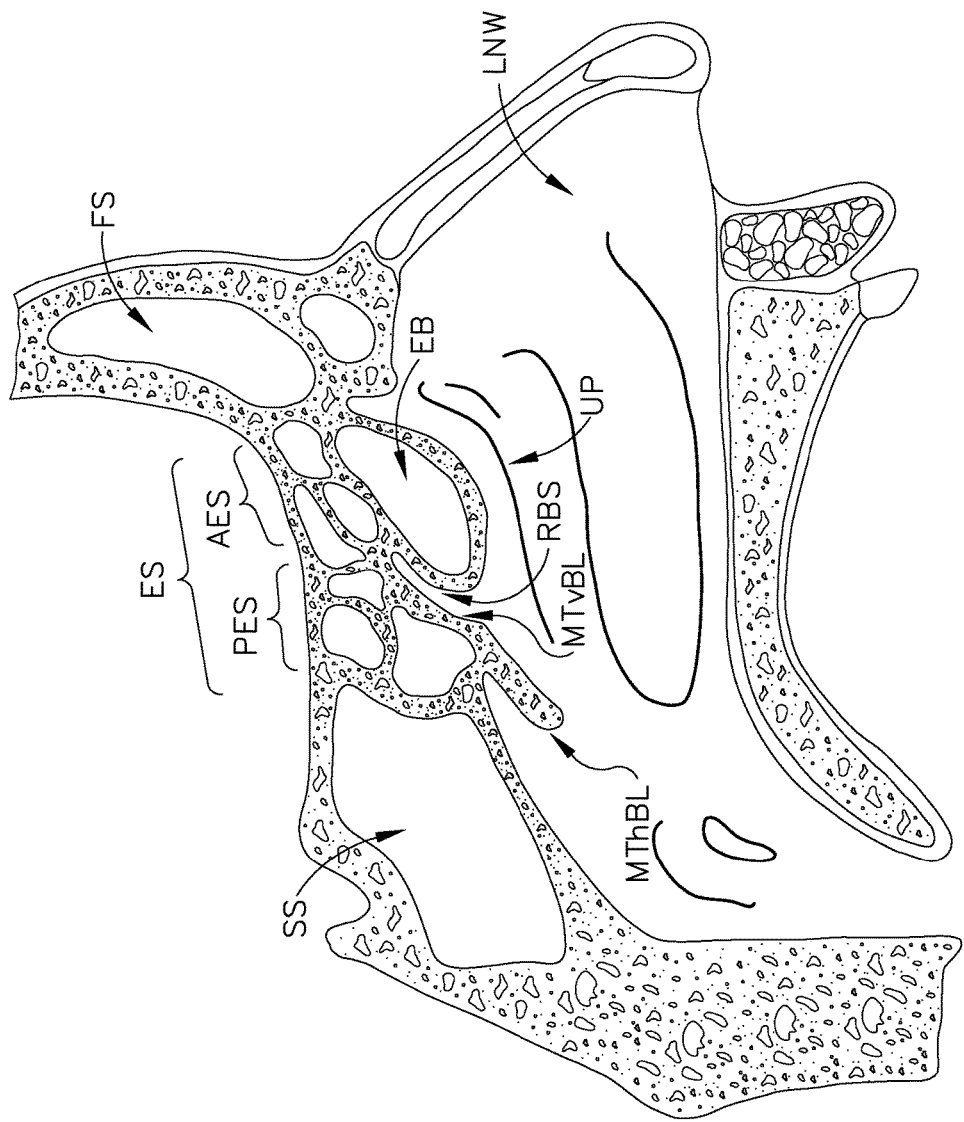
FIG. 6 depicts a left sagittal cross-sectional view of a portion of a human head, showing paranasal sinus structures.

FIG. 6 shows a left sagittal cross-sectional view of a portion of a human head, which includes a sphenoid sinus (SS), ethmoid sinus (ES), frontal sinus (FS), middle turbinate horizontal basal lamella (MThBL), middle turbinate vertical basal lamella (MTvBL), uncinate process (UP), and lateral nasal wall (LNW). The ethmoid sinus (ES) comprises a set of sinus cells that may be categorized as anterior ethmoid sinus (AES) cells and posterior ethmoid sinus (PES) cells. The ethmoid bulla (EB) is the largest ethmoid sinus (ES) cell, and is generally inferior and anterior to the other cells of the ethmoid sinus (ES). The posterior wall of the ethmoid bulla (EB) and the middle turbinate vertical basal lamella (MTvBL) together define a retrobullar space (RBS). It should be understood that anatomical variation in the human is such that this retrobullar space (RBS) may or may not be present in a given individual.

The ethmoid sinus (ES) includes ostia (not shown) for providing fluid communication to and from the cells of the ethmoid sinus (ES) and the nasal cavity. For instance, ostia may provide fluid paths for cells within the anterior ethmoid sinus (AES), cells within the posterior ethmoid sinus (PES), and the ethmoid bulla (EB). In some instances, suprabullar cells of the ethmoid sinus (ES) drain into the ethmoid bulla (EB). Some suprabullar cells may drain directly into the retrobullar space (RBS). The ethmoid bulla (EB) may itself provide fluid communication with the nasal cavity via one or more ostia, such that the ethmoid bulla (EB) may provide a fluid communication path between the other ethmoid sinus (ES) cells (that drain into the ethmoid bulla (EB)) and the nasal cavity. For instance, the ethmoid bulla (EB) may provide fluid communication through an ostium at the retrobullar space (RBS). The fluid communication paths provided by ostia may allow the entry of air and liquids (e.g., medications); while also allowing drainage of mucus. In some instances, the ostia may become blocked, may become functionally closed due to mucosal thickening, or may otherwise not provide sufficient fluid communication. In addition or in the alternative, the configuration of the retrobullar space (RBS) may impede flow through the ostium of the ethmoid bulla (EB).

The anatomy of the ethmoid sinus (ES) may make it impractical to perform a dilation procedure on ostia of the ethmoid sinus (ES) using dilation catheter system (10) to improve fluid communication within the ethmoid sinus (ES). This may lead some operators to perform an ethmoidectomy, which is an invasive procedure that involves removal of ethmoid sinus (ES) portions (e.g., tissue and bone) using an instrument such as a debriding instrument. This kind of procedure may be somewhat crude and inelegant, resulting in removal of significant amounts of mucosa that might otherwise benefit the patient. Ethmoidectomy procedures may also have risks of inadvertent damage to optic nerves, damage to orbital muscles, damage to olfactory bulbs, damage to other anatomical structures, and even leakage of cerebrospinal fluid. Even in successful ethmoidectomies, the patient may need to return for several follow-up debridements. It may therefore be desirable to improve fluid communication from within the ethmoid sinus (ES) to the nasal cavity without resorting to a procedure like an ethmoidectomy. In some instances, this may involve implantation of a port in one or more cells of the ethmoid sinus (ES). Several merely illustrative examples of such ports are described in greater detail below, while other examples will be apparent to those of ordinary skill in the art in view of the teachings herein.

FIGS. 7A-10B show an exemplary instrument (100) that may be used to pierce an opening in the ethmoid bulla (EB). Instrument (100) of this example includes a shaft assembly (102) that may be introduced through the patient's nose, for example, for accessing the ethmoid bulla (EB). Shaft assembly (102) includes a first shaft member (104) which, in the example shown, comprises a tubular cutter. Shaft assembly (102) further includes a second shaft member (106) which, in the example shown, comprises an outer sheath (106) surrounding the tubular cutter (104). Tubular cutter (104) includes a proximal end portion (108) and a distal end portion (110) including a distal cutting feature (112). Cutting feature (112) is an annular cutting edge that extends along a plane that is perpendicular to a longitudinal axis of tubular cutter (104) in this example. In some other versions, cutting feature (112) includes a cutting edge (not shown) extending along, a plane that is obliquely oriented relative to longitudinal axis of tubular cutter (104). In the present example, cutting feature (112) is beveled to provide a sharp edge. In other versions, cutting feature (112) is hollow ground or is otherwise configured to provide a sharp edge that is operable to cut through a sinus wall. Outer sheath (106) includes a proximal end portion (114), a distal end portion (116) defining a distal edge (118), and a lumen (120) extending between the proximal and distal end portions (114, 116). In the present example, at least a portion of tubular cutter (104) is received within lumen (120) of outer sheath (106) such that tubular cutter (104) is positioned radially inward and generally coaxially relative to outer sheath (106). Tubular cutter (104) is configured to move or slide relative to outer sheath (106) such that at least distal end portion (110) of tubular cutter (104) may extend distally relative to distal edge (118) the outer sheath (106). Therefore, distal cutting feature (112) of tubular cutter (104) may be exposed when tubular cutter (104) moves distally relative to outer sheath (106). At least a portion of each of the tubular cutter (104) and outer sheath (104, 106) may be flexible in order to traverse a variety of internal anatomical structures, such as the nasal cavity and paranasal sinuses. Distal edge (118) in the present example is blunt or otherwise non-sharpened, and could include a plastic or elastomeric tip to minimize risk of inadvertent trauma to tissue in the nasal cavity during insertion of shaft assembly (102).

Shaft assembly (102) is coupled to a body (122) and other features that enable the tubular cutter (104) to move relative to the outer sheath (106). Body (122) includes a proximal end portion (124) defining at least part of a handle member (126) and a distal end portion (128) having a pair of opposing prongs (130) and a distal face (132). Prongs (130) and distal face (132) define at least a portion of a grounding feature (134) that is sized and positioned to engage one or more external anatomical structures adjacent to the nose or nostril of a patient (e.g., calumella of the nasal septum and the alar rim or other regions of the anterior nares, etc.) when at least the distal portion of the shaft assembly (102) is inserted into the nostril. Thus, body (122) cooperates with external regions of the patient's nose to provide a mechanical ground during operation of instrument (100), thereby helping to stabilize shaft assembly (102) in the patient's paranasal cavity. Body (122) further includes an elongate opening (136) between the proximal and distal end portions (124, 128) of body (122). Elongate opening (136) is generally rectangular in cross section and is defined in part by a proximal face (138) and a distal face (140). Distal face (140) is in communication with a bore (142) in proximal portion (124) of body (122). Bore (142) extends from the proximal face (138) (136) and through body (122) towards the proximal end portion (124) of body (122). Proximal face (138) is in communication with an aperture (144) that extends through the body (122), particularly between proximal face (138) and distal face (132) of body (122). In the example shown, outer sheath (106) is fixed relative to distal face (132) such that lumen (120) of outer sheath (106) is oriented coaxially relative to aperture (144).

In some versions, shaft assembly (102) may be configured to be adjusted such that at least the outer sheath (106) may be adjusted relative to body (122) in order to account for anatomical differences of different patients. In that regard, at least the outer sheath (106) may be configured to move proximally relative to body (122) in order to essentially shorten the effective length of shaft assembly (102). Alternatively, at least the outer sheath (106) may be configured to move distally to essentially lengthen shaft assembly (102). In some such versions (not shown) at least the outer sheath (106) may be biased proximally towards the body (122), and movable in the proximal direction; or, biased distally away from the body (122) and movable in the distal direction. In such examples, the shaft assembly (102) may then include a ratchet or other type of retention mechanism (not shown) that allows the outer sheath (106) to be maintained in a position other than its initial, biased position. For example, outer sheath (106) may be coupled to a resilient member such as a spring (not shown) that biases the outer sheath (106) into a biased position relative to the body (122). Where the user desires to move the outer sheath (106) away from the biased position, the user may move at least the outer sheath (106) in a direction opposite of the biasing force, and outer sheath (106) may be retained in a position by a ratchet or other mechanism. In such examples, aperture (144) may be sized in order to allow for proximal movement of outer sheath (106) relative to body (122).

Instrument (100) further includes a guide rod (146) extending from a proximal end (148) of bore (142) to aperture of body (122), and a spring (150). More particularly, a first end (152) of spring (150) is fixedly coupled to proximal face (148) that is adjacent to bore (142) and is placed around, and positioned generally coaxially relative to, guide rod (146). In the example shown, tubular cutter (104) includes a lumen (154) for receiving at least a portion of guide rod (146) such that tubular cutter (104) may slide along guide rod (146). In order to assemble instrument (100), in one exemplary method of assembly, tubular cutter (104) is directed through lumen (120) of outer sheath (106) until a proximal end (108) of tubular cutter (104) reaches guide rod (146). Guide rod (146) is permitted to enter lumen (154) of tubular cutter (104), thus allowing further proximal movement of the tubular cutter (104) relative to the body (122) and the outer sheath (106). An actuator feature (156) is fixedly coupled to the tubular cutter (104) by methods such as plastic welding, adhesives, interference fit, snap fit, etc., for example, once a distal portion (110) of tubular cutter (104) is coincident with opening (136). Actuator feature (156) is also fixedly coupled with a second end (157) of spring (150) by methods such as adhesives or other bonding or assembly methods. Thus, the tubular cutter (104) is operably coupled to spring (150).

Instrument (100) of the present example further includes an optional dashpot assembly (158), which is operably coupled to actuator feature (156). Dashpot assembly (158) comprises a cylinder (159) having a distal orifice (160a) and a proximal opening (160b) with a chamber (161) extending therebetween. Dashpot assembly (158) further includes a rod (162a) and a plunger (162b) at a distal end of rod (162a). In the present example, rod (162a) is fixedly coupled to actuator feature (156). Various suitable structures and methods that may be used couple rod (162a) with actuator feature (156) will be apparent to those of ordinary skill in the art in view of the teachings herein. Cylinder (159) is fixedly coupled to the distal end portion (128) of body (122). Plunger (162b) and at least a portion of rod (162a) are received within, and are movable relative to, chamber (161) of cylinder (159). Plunger (162b) is snugly yet slidably fit in chamber (161).

In an alternative example, rather than including a lumen (154) for receiving and sliding along guide rod (146), tubular cutter (104) and/or shaft assembly (102) may include additional components that operably couple the tubular cutter (104) with the actuator feature (156) and the spring (150). By way of example, an alternative tubular cutter (not shown) may include a shorter length than that shown in the present example. In this alternative example, the shorter tubular cutter (not shown) may be coupled to an extension member (that may or may not be part of the shaft assembly (102)). Extension member (not shown) may include a cavity or lumen that allows the extension member to receive the guide rod (146), thus enabling the extension member to move along the guide rod (146). In this alternative example, actuator feature (156) may be coupled to the spring (150) in a similar manner described above. Similarly, the actuator feature (156) may be coupled to the extension member in a similar manner as described with respect to the tubular cutter (104) of the example described above.

In the example shown in FIGS. 7A-10B, actuator feature (156) is positioned relative to body (122) such that at least a portion of actuator feature (156) extends transversely from body (122) above a top surface (162) of body (122) of instrument (100). Therefore, actuator feature (156) may be accessed by a clinician in order to advance actuator feature (156) in the distal direction. In the example shown, actuator feature (156) is shown to be generally rectangular in cross-section, but may include other configurations or features in alternative examples. For example, actuator feature (156) may include contours, textures, coatings, or other features (not shown) that may improve a clinician's grip (i.e., of a finger or thumb) on the actuator feature (156) as the actuator feature (156) is utilized. Similarly, proximal portion (124) of body (122) may include contours, textures, coatings, or other features (not shown) that may improve a clinician's grip on the handle member (126) as the clinician uses instrument (100).

Figure 8:
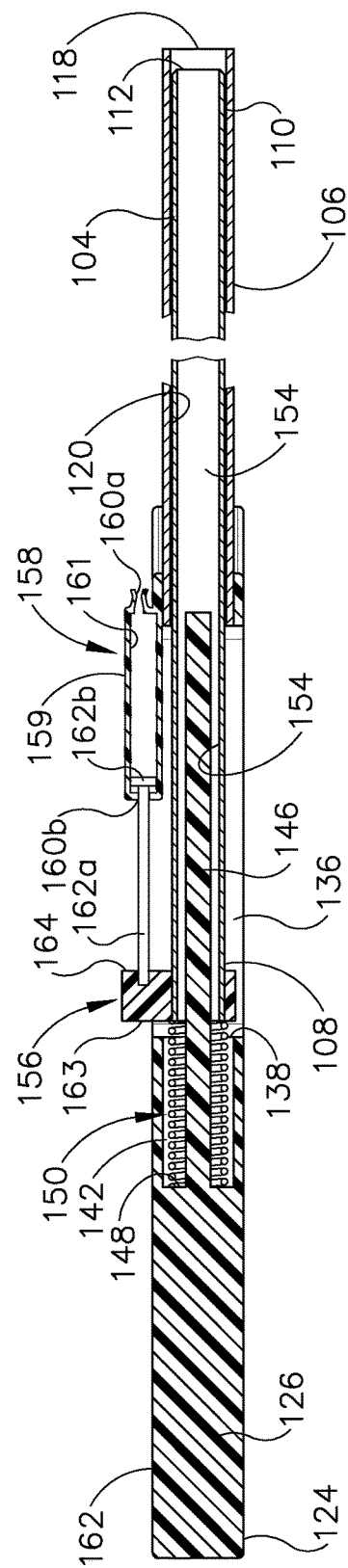
FIG. 8 depicts a cross-sectional view of the instrument of FIG. 7A, taken along line 8-8 of FIG. 7A, with the cutting feature in the retracted position.
Figure 9:
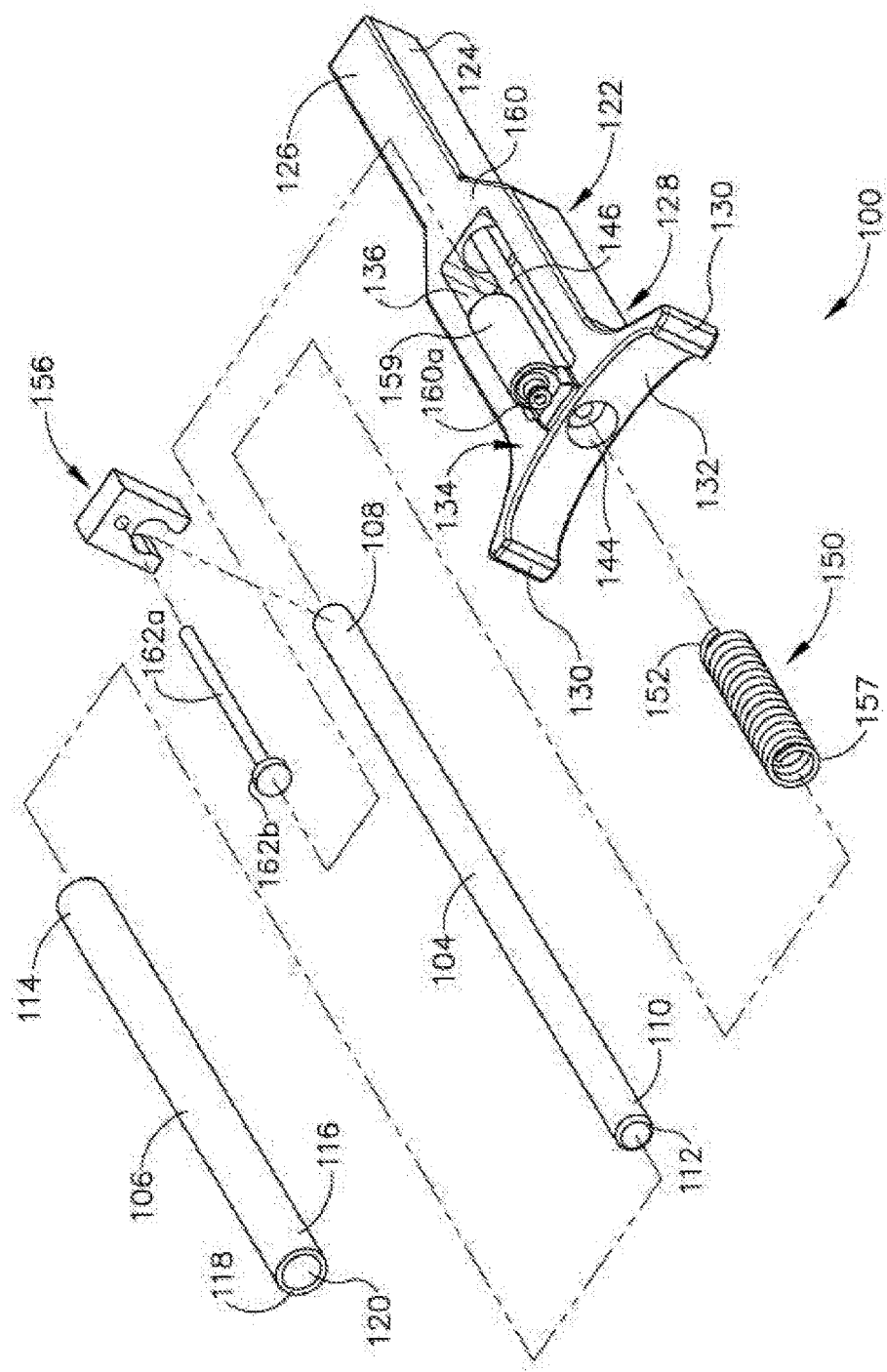
FIG. 9 depicts a exploded perspective view of the instrument of FIG. 7A.

Spring (150) is biased to urge the tubular cutter (104) proximally relative to the body (122) and also relative to the outer sheath (106). Therefore, in the present example, spring (150) acts as a dampener to resist distal advancement of the tubular cutter (104) relative to the outer sheath (106). In the example shown, spring (150) is a tension spring that, due to its position (proximal relative to actuator feature (156)) and manner of coupling with the actuator feature (156), biases actuator feature (156) and tubular cutter (104) in the proximal direction. In an alternative example (not shown), however, spring (150) may be a compression spring configured and positioned (distally relative to actuator feature (156)) to bias the actuator feature (156) and tubular cutter (104) in the proximal direction. By way of example, rather than being fixed to a proximal portion (163) of actuator feature (156) and proximal face (148) of bore (142) (as shown in FIG. 8) the compression spring (not shown) of some alternative examples may be fixed to a distal portion (164) of actuator feature (156) and distal face (140).

In some examples, instrument (100) may include structures and/or features in addition to spring (150), or as an alternative to spring (150), that act as a dampener to resist advancement of the tubular cutter (104) relative to the outer sheath (106). In that regard, in the example shown, in addition to spring (150), instrument (100) includes the optional dashpot assembly (158) that provides friction resisting advancement of the tubular cutter (104) relative to the outer sheath (106). In the example shown, dashpot assembly (158) utilizes air pressure to provide resistance. It should be understood that various features of dashpot assembly (158) may be varied to modify the resistance provided by dashpot assembly (158). For instance, the size of the distal orifice (160a) may be larger or smaller than shown; or may be adjustable during use to allow changes in the resistive properties of the dashpot assembly (158). Other ways of altering the resistive and other properties (i.e., time dependent properties) of the dashpot assembly (158) will be apparent to those of ordinary skill in the art in view of the teachings herein. In some alternative examples, dashpot assembly (158) may utilize hydraulic or liquid pressure rather than air.

Some versions of instrument (100) may include a dashpot assembly (158) according to the above or alternative teachings, but omit spring (150) and/or other resilient members that bias the tubular cutter (104) in the proximal direction. In some such versions, dashpot assembly (158) may provide friction resisting distal advancement of the tubular cutter (104) relative to the outer sheath (106). Therefore, in those and other examples, dashpot assembly (158) may also prevent sudden changes in velocity of the tubular cutter (104). In versions without spring (150), the operator may have to retract the tubular cutter (104) after proximally advancing the tubular cutter (104) by actuating the actuating feature (156) in the proximal direction. In some versions of instrument including dashpot assembly (158), dashpot assembly (158) may provide unrestricted proximal movement of tubular cutter (104) relative to the outer sheath (106), while providing some degree of resistance to distal movement of tubular cutter (104) relative to the outer sheath (106), thereby preventing sudden changes in velocity of the tubular cutter (104). In some alternative versions, dashpot assembly (158) may be configured to provide resistance to both proximal and distal movement of the tubular cutter (104) relative to outer sheath (106). In further alternative versions, dashpot assembly (158) may be mounted on a different portion of body (122), such as on or near handle member (126); and be mounted to a proximal portion (163) of actuator feature (156). Various other suitable forms that dashpot assembly (158) may take, as well as various ways in which instrument (100) may incorporate a dashpot in addition to or in lieu of spring (150), will be apparent to those of ordinary skill in the art in view of the teachings herein. As yet another merely illustrative variation, spring (150) may be substituted with an elastic band or other kind of resilient member(s).

The tubular cutter (104) is resiliently biased to a first position (FIGS. 7A, 10A, for example) where the cutting feature (112) is spaced proximally from a distal edge (118) of the outer sheath (106). Alternatively, in the first position, the cutting feature (112) is essentially flush with the distal edge (118) of outer sheath (106). When the actuator feature (156) is actuated or slid in the distal direction, the tubular cutter (104) may be moved to a second position (FIGS. 7B, 10B, for example) where the cutting feature (112) extends distally relative to the distal edge (118). In order to control the amount of movement of the tubular cutter (104) relative to the outer sheath (106), spring (150) is configured to allow the tubular cutter (104) to move a predetermined distance (d) relative to the outer sheath (106). In addition or in the alternative, dashpot assembly (158) (where provided) may also be configured to allow tubular cutter (104) to move a predetermined distance (d) relative to the outer sheath (106). For example, the interaction between plunger (162b) and the inside distal portion of chamber (161) may also act to limit the distal movement of tubular cutter (104) relative to outer sheath (106). As shown in FIG. 7B, a distance (d) is measured as the distance between distal edge (118) of outer sheath (106) and the end of cutting feature (112) of tubular cutter (104). The interaction between actuator feature (156) and distal face (138) may also act to limit the distal movement of the tubular cutter (104) relative to the outer sheath (106).

Figure 10A:
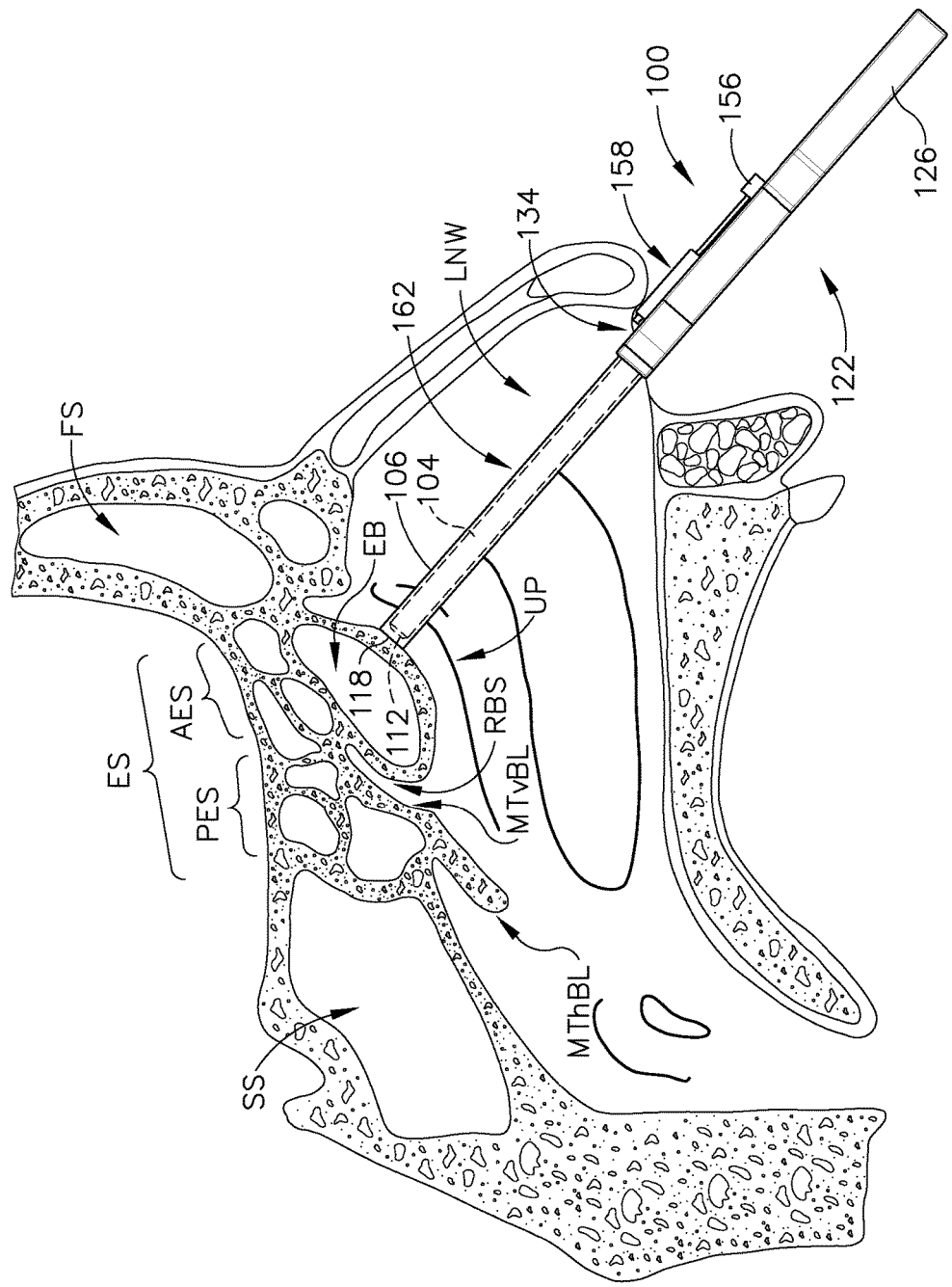
FIG. 10A depicts a left sagittal cross-sectional view of a portion of a human head, with a distal portion of the instrument of FIG. 7A placed adjacent to the anterior wall of the ethmoid bulla, and a cutting feature of the instrument in a retracted position.
Figure 10B:
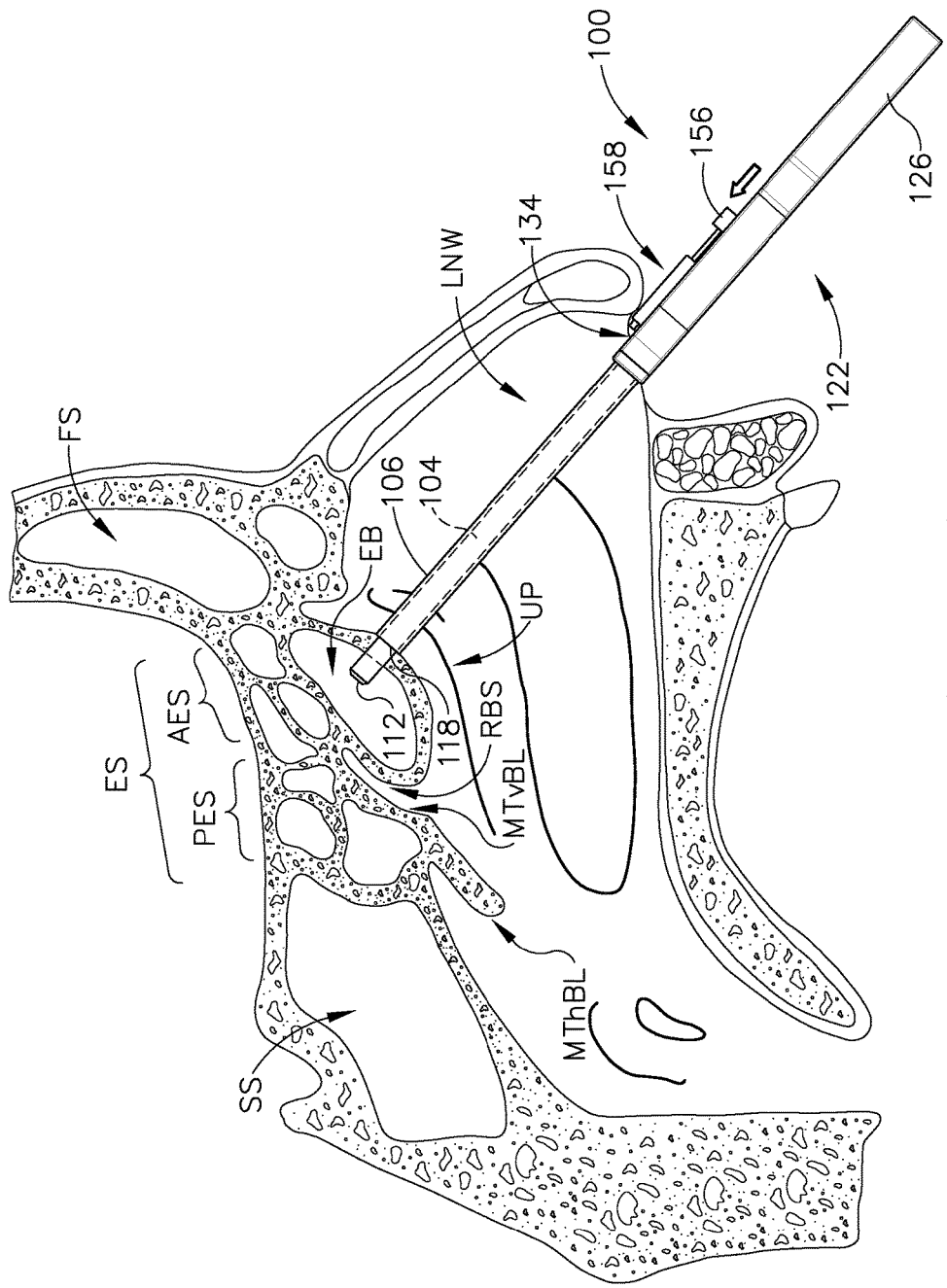
FIG. 10B depicts a left sagittal cross-sectional view of a portion of a human head, with a distal portion of the instrument of FIG. 7A placed adjacent to the wall of the ethmoid bulla, and a cutting feature of the instrument in an extended position piercing the anterior wall of the ethmoid bulla.
Figure 10C:
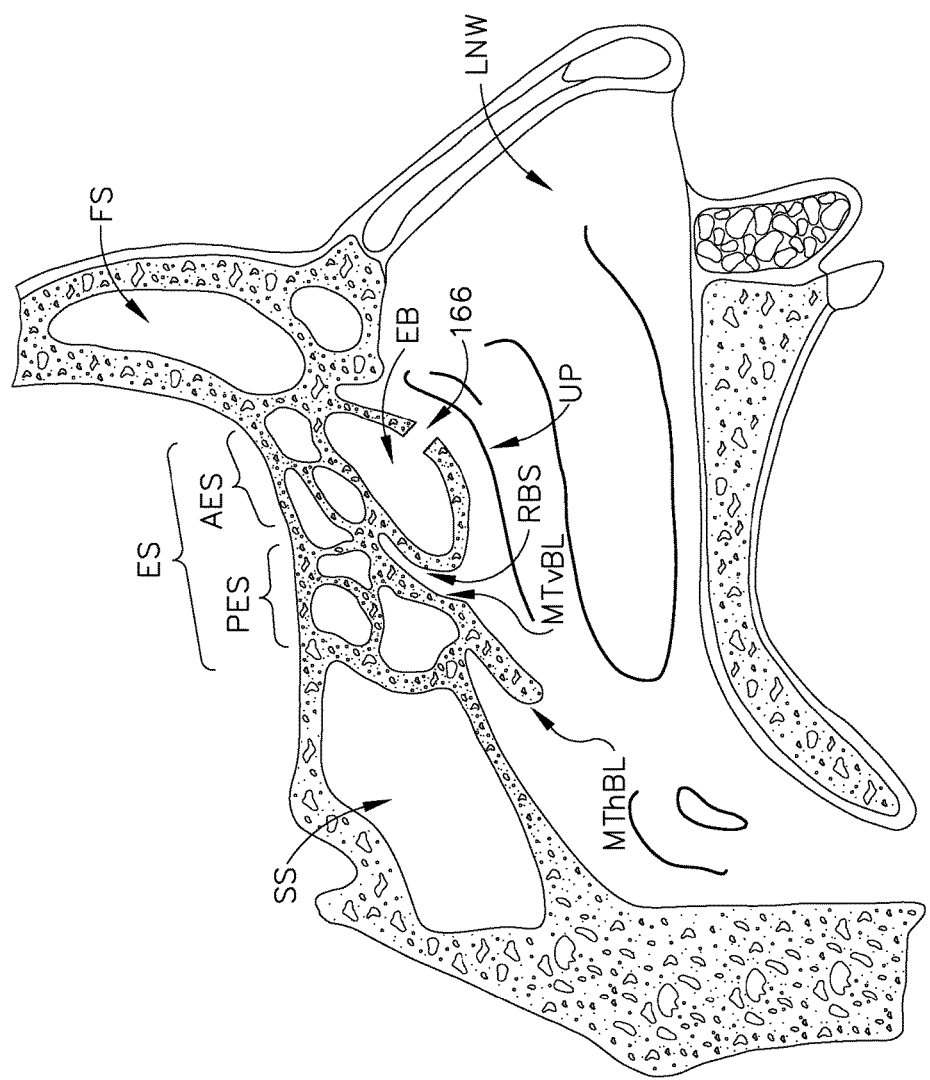
FIG. 10C depicts a left sagittal cross-sectional view of a portion of a human head, showing the pierced anterior wall of the ethmoid bulla.

Referring to FIGS. 10A-B, shaft assembly (102) of instrument (100) may be introduced through the patient's nose (in this case, the patient's right nostril) until grounding feature (134) abuts against the patient's external anatomical structure, more specifically, against a position adjacent and inferior to the patient's nostril (e.g., calumella of the nasal septum and the alar rim or other regions of the anterior nares, etc.). Preferably, the shaft assembly (102) is sized such that when grounding feature (134) abuts the external anatomical structure adjacent to the nostrils, distal edge (118) of outer sheath (106) is positioned at, and abuts, an anterior/inferior wall of the ethmoid bulla (EB). However, as discussed above, at least the outer sheath (106) of the shaft assembly (102) may be moved proximally relative to the body (122) once the distal portion of shaft assembly (102) is inserted into the nostril, in order to account for greater or lesser distances between the nostrils and one or more internal anatomical structures, such as an anterior inferior wall of the ethmoid bulla (EB). Instrument (100) may be positioned using visualization from endoscope (60) described above and/or from some other device.

Once distal edge (118) of outer sheath (106) is positioned at the ethmoid bulla (EB) and grounding feature (134) is placed against the patient's external anatomical structure to provide a mechanical ground and stabilize instrument (100), the clinician may actuate the actuator feature (156) such that tubular cutter (104) is advanced distally. Therefore, as tubular cutter (104) is moved distally, distal cutting feature (112) is advanced against the wall of the ethmoid bulla (EB). Cutting feature (112) is configured to pierce the wall of the ethmoid bulla (EB) without shattering the wall of the ethmoid bulla (EB). In other words, the wall of the ethmoid bulla (EB) remains intact except for the opening (166) created by instrument (100), with such an opening (166) (FIG. 10C) being approximately the same size as the outer diameter tubular cutter (104).

Due to configuration of the instrument (100) described herein, tubular cutter (104) travels less than or equal to distance d past distal edge (118) of outer sheath (106), and outer sheath (106) is substantially prevented from moving relative to the patient's anatomy, due at least in part to grounding feature (134). Once the ethmoid bulla (EB) has been pierced, the operator may simply release actuator (156) after tubular cutter (104) has been advanced, allowing spring (148) to return tubular cutter (104) to the proximal position. Alternatively, (e.g. when a dashpot is used instead of a spring (148)), operator could slide actuator (156) proximally. As yet another example, the operator could withdraw entire shaft assembly (102) without first retracting tubular cutter (104) relative to outer shaft (106).

FIG. 11 shows an exemplary force-distance plot of two different instruments for piercing the ethmoid bulla (EB) in, for example, the manner described herein. Using the exemplary instrument (100) as an example, spring (150) acts as a dampener to increase the initial force required to pierce the ethmoid bulla (EB), but results in a more controlled distance. A force-distance plot associated with exemplary instrument (100) is labeled with reference numeral 168, while a force-distance plot labeled with an exemplary alternative instrument (which omits spring (148) or any other dampening element) is labeled with reference numeral 170. Referring to plot (168), at least some of the force with which the actuator feature (156) is acted upon is translated to the external anatomical structure, instead of the wall of the ethmoid bulla (EB), due to the interaction between the grounding feature (134) and the external anatomical structure. Thus, exemplary instrument (100) therefore provides a controlled motion of the tubular cutter (104) and prevents an opening with ragged edges, a larger opening than intended in the wall of the ethmoid bulla (EB), or unintended trauma to the ethmoid structure behind the anterior wall of the ethmoid bulla (EB). On the other hand, plot (170) shows that a high force is required to push through the ethmoid bulla (EB). Once the puncture is initiated, the high force that the clinician applied to create the puncture is translated into an uncontrolled movement. This movement typically results in the clinician moving the instrument deeper into the anatomy than is desired or expected, which may lead to an opening with ragged edges, a larger opening than intended, or unintended trauma to the ethmoid structure behind the anterior wall of the ethmoid bulla (EB). Spring (148) absorbs forces that would otherwise cause this movement upon penetration of the ethmoid bulla (EB). It should be understood that versions of instrument (100) that include dashpot assembly (158) may provide a force plot that is similar to plot (168) in that the force changes less over distance than the change shown in plot (170); yet the force plot provided by dashpot assembly (158) may be even flatter than plot (168) due to the fact that the resistance provided by dashpot assembly (158) does not vary with the distance traveled by actuator feature (156).

It should be understood that instrument (100) may be utilized to create one or more punctures or holes in the anterior wall or other walls/structures of the ethmoid sinus. Additionally or alternatively, instrument (100) may be utilized to create one or more punctures in various other structures of the paranasal sinuses (e.g. another wall associated with the ethmoid sinus, a wall of the frontal sinus, a wall of the sphenoid sinus, etc.). After instrument (100) has pierced the ethmoid bulla (EB), a port or another instrument or device (not shown) may be positioned within the opening (166) created in the wall of the ethmoid bulla (EB) by the cutting feature (112). Such a port or instrument may be in constructed and operable accordance with at least some of the teachings from U.S. Pub. No. 2014/0277043, published Sep. 18, 2014, now U.S. Pat. No. 9,629,684, issued Apr. 25, 2017, the disclosure of which is incorporated by reference herein. It should be understood that, once opening (166) has been created, opening (166) enables the substantially free communication of air/mucus/etc. into and out of the ethmoid bulla (EB). Opening (166) thus serves as a substitute or supplemental ostium for the ethmoid bulla (EB). In some instances, the patient may be instructed to periodically self-administer medications or other fluids within their nose after opening (166) has been created. By way of example only, such fluids/medications may include saline, a combination of saline and a surfactant, an anti-inflammatory (e.g., mometasone, etc.), an antibiotic, an anti-fungal, and/or various other kinds of fluids/medications, including combinations thereof. Opening (166) may provide a substantially clear path for such fluids/medications to reach the mucosa within the ethmoid bulla (EB), in addition to providing a vent/drainage path for the ethmoid bulla (EB). In other words, the presence of opening (166) may provide substantially greater communication of the administered fluids/medications to the ethmoid bulla (EB) than the communication that would be provided in the absence of opening (166).

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other.

Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning, and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An instrument, comprising:
(a) a shaft assembly, wherein the shaft assembly comprises:
(i) a first shaft member, wherein the first shaft member includes a distal cutting feature, and
(ii) a second shaft member, wherein the first shaft member is slidable relative to the second shaft member, wherein the second shaft member comprises a distal end portion having a distal edge;
wherein at least a distal portion of the shaft assembly is sized to fit through a nostril;
wherein the first shaft member is movable between a first position where the distal cutting feature is flush with or spaced proximally from the distal edge and a second position where the distal cutting feature extends distally relative to the distal edge;
(b) a body, wherein at least a portion of the shaft assembly extends distally relative to the body, wherein the body comprises a grounding feature, wherein the grounding feature includes a pair of prongs sized and positioned to engage one or more external anatomical structures adjacent to the nostril; and
(c) a dampener, wherein the dampener is configured to resist yet permit advancement of the first shaft member relative to the second shaft member.

2. The instrument of claim 1, wherein: the second slidable relative to the body.

3. The instrument of claim 2, wherein: the second shaft member is biased distally relative to the body.

4. The instrument of claim 1, further comprising: an actuator feature in communication with the dampener and the first shaft member.

5. The instrument of claim 4, wherein: the dampener is configured to urge the first shaft member proximally relative to the second shaft member when the actuator feature is actuated with a predetermined amount of force.

6. The instrument of claim 5, wherein: the dampener is configured to urge the first shaft member proximally relative to the second shaft member when the actuator feature is actuated with a predetermined amount of force in the distal direction.

7. The instrument of claim 5, wherein: the dampener is configured to urge the first shaft member proximally relative to the second shaft member when the actuator feature is actuated with a predetermined amount of force in the proximal direction.

8. The instrument of claim 1, wherein: the dampener is configured to allow the first shaft member to move a predetermined distance relative to the second shaft member.

9. The instrument of claim 1, wherein: the grounding feature is contoured to complement the configuration of the one or more external anatomical structures.

10. The instrument of claim 9, wherein: the grounding feature is contoured to match the configuration of one or more anatomical structures of the nose or adjacent to the nose.

11. The instrument of claim 1, wherein: the cutting feature includes a generally frustoconically shaped portion.

12. The instrument of claim 1, wherein the cutting feature is defined at least in part by a tapered portion at a distal end portion of the first shaft member.

13. The instrument of claim 1, wherein: at least a portion of the shaft assembly is flexible.

14. The instrument of claim 1, wherein: the dampener further comprises a hydraulic feature.

15. An instrument, comprising:
(a) a shaft assembly, wherein the shaft assembly comprises:
(i) a first shaft member, wherein the first shaft member includes a distal cutting feature, wherein the distal cutting feature comprises an annular cutting edge that extends along a plane that is perpendicular to a longitudinal axis of the first shaft member, and
(ii) a second shaft member, wherein the first shaft member is slidable relative to the second shaft member, wherein the second shaft member comprises a distal end portion having a distal edge;
wherein at least a distal portion of the shaft assembly is sized to fit through a nostril;
wherein the first shaft member is movable between a first position where the distal cutting feature is flush with or spaced proximally from the distal edge and a second position where the distal cutting feature extends distally relative to the distal edge,
(b) a body, wherein the shaft assembly extends distally relative to the body, wherein the second shaft member is slidable relative to the body, wherein the body comprises a grounding feature, wherein the grounding feature is sized and positioned to engage one or more external anatomical structures adjacent to the nostril; and
(c) a dampener, wherein the dampener is biased to urge the first shaft member proximally relative to the second shaft member.

16. An instrument, comprising:
(a) a shaft assembly, wherein the shaft assembly comprises:
(i) a first shaft member, wherein the first shaft member includes a distal cutting feature, and
(ii) a second shaft member, wherein the first shaft member is slidable relative to the second shaft member, wherein the second shaft member comprises a distal end portion having a distal edge;
wherein at least a distal portion of the shaft assembly is sized to fit through a nostril;
wherein the first shaft member is movable between a first position where the distal cutting feature is flush with or spaced proximally from the distal edge and a second position where the distal cutting feature extends distally relative to the distal edge;
(b) a body, wherein at least a portion of the shaft assembly extends distally relative to the body, wherein the body comprises a grounding feature, wherein the grounding feature sized and positioned to engage one or more external anatomical structures adjacent to the nostril; and
(c) a dampener, wherein the dampener comprises a dashpot assembly configured to resist yet permit advancement of the first shaft member relative to the second shaft member.

17. The instrument of claim 16, wherein the distal cutting feature comprises an annular cutting edge.

18. The instrument of claim 16, wherein the second shaft member is slidable relative to the body.

19. The instrument of claim 16, further comprising an actuator feature in communication with the dampener and the first shaft member.

* * * * *